US009351810B2

(12) United States Patent
Moon

(10) Patent No.: US 9,351,810 B2
(45) Date of Patent: May 31, 2016

(54) MAXILLARY SKELETAL EXPANDER USING MINI-SCREW

(71) Applicant: Biomaterials Korea Inc., Seoul (KR)

(72) Inventor: Won Moon, Fullerton, CA (US)

(73) Assignees: Won Moon, Los Angeles, CA (US); Biomaterials Korea Inc., Seoul (KR)

( * ) Notice: Subject to any disclaimer, the term of this patent is extended or adjusted under 35 U.S.C. 154(b) by 0 days.

(21) Appl. No.: 14/308,903

(22) Filed: Jun. 19, 2014

(65) Prior Publication Data

US 2015/0056566 A1  Feb. 26, 2015

(30) Foreign Application Priority Data

Aug. 26, 2013 (KR) .................. 10-2013-0100858

(51) Int. Cl.
*A61C 19/00* (2006.01)
*A61C 7/10* (2006.01)
(52) U.S. Cl.
CPC ........................................ *A61C 7/10* (2013.01)
(58) Field of Classification Search
CPC ........................................................ A61C 7/10
USPC ............................................................. 433/7
See application file for complete search history.

(56) References Cited

U.S. PATENT DOCUMENTS

2013/0252195 A1* 9/2013 Popat ............................ 433/24

OTHER PUBLICATIONS

Integral. (n.d.). Dictionary.com Unabridged. Retrieved Feb. 24, 2015, from Dictionary.com website: http://dictionary.reference.com/browse/integral.*
Moon, Won, "New Revolutionary Findings: Changes in Skeletal Morphology and Airways with Micro-Implant Assisted Rapid Palatal Expanders (MARPE)", 5th World Implant Orthodontic Conference, Nov. 13-15, 2013, Phuket, Thailand, www.wioc2013.com, pp. 1-3.
Unknown, "KSO Proposal of Extraction-Nonextraction Treatment Guideline", Dental Today, Korean Society of Orthodontists, 11th symposium of Revisits to Extraction vs Nonextraction, Seoul, Jun. 20, 2013, Korean Translation, pp. 1-2.
Unknown, "KSO Proposal of Extraction-nonextraction Treatment Guidelines", Dental Today, Korean Society of Orthodontists, 11th symposium of Revisits to Extraction vs Nonextraction, Seoul, Jun. 20, 2013, English Translation, pp. 1-2.

* cited by examiner

*Primary Examiner* — Heidi M Eide
(74) *Attorney, Agent, or Firm* — Murphy, Bilak & Homiller, PLLC

(57) ABSTRACT

A maxillary skeletal expander includes a pair of bodies, an extending screw adjusting a space between the pair of bodies, guide rails having both sides inserted into the pair of bodies and guiding a movement of the bodies, a key hole integrally formed with the extending screw, screw insertion portions integrally formed with the bodies and having screw insertion holes guiding mini-screws implanted to an upper jaw, arms having one end fixed to the bodies and the other end extending toward teeth, and a teeth fixing part integrally formed with the arms and fixed to teeth of a patient.

3 Claims, 3 Drawing Sheets

MAXILLARY SKELETAL EXPANDER USING MINI-SCREW

PRIORITY CLAIM

The present application claims priority to Korean Patent Application No. 10-2013-0100858 filed on 26 Aug. 2013, the content of said application incorporated herein by reference in its entirety.

TECHNICAL FIELD

The present invention relates to a maxillary skeletal expander.

BACKGROUND

In general, a maxillary skeletal expander, a device used for a treatment of a patient whose upper jaw is less developed than the lower jaw, serves to expand the upper jaw to facilitate a treatment. Facial bones act like puzzle making, so bones may be easily moved during a growth period, and an upper jaw is composed of several bones engaging with one another, rather than being a single bone. If an upper jaw is too small to accommodate permanent tooth, a bone portion in the center of a ceiling of a mouth may be outstretched to expand a maxillary arch itself.

FIG. 1 is a view illustrating a conventional art maxillary skeletal expander. The related art maxillary skeletal expander is fixed to a maxillary arch A and includes a pair of bodies 1, arms 2 fixed to the bodies 1, an extending screw 3 adjusting a space between the pair of bodies 1, a guide rail 4 guiding a movement of the bodies 1 when a space between the bodies 1 is adjusted, key a hole 5 formed in the extending screw 3 allowing the extending screw 3 to rotate when a rotational key is inserted thereinto and rotated, and a fixing part 6 combined with the arms 2 so as to be fixed to the teeth B of a patient. When a key is inserted into the key hole 5 to rotate the extending screw 3, the bodies 1 are moved in a direction toward the teeth B on both sides and a space between the bodies 1 is opened, whereby the maxillary skeletal expander expands the fixed upper jaw. However, in the case of the related art maxillary skeletal expander, since the fixing part 5 is fixed to the teeth B, rather than to the maxillary arch A, the maxillary arch A is not expanded and only the teeth B are gapped in many cases.

In order to solve the problem, a maxillary skeletal expander using mini-screws has been developed. In this case, the maxillary skeletal expander is fixed to the maxillary arch A with screws. FIG. 2 is a view illustrating a related art maxillary skeletal expander using mini-screws. The maxillary skeletal expander using mini-screws includes a pair of bodies 10, arms 20 fixed to the bodies 10, an extending screw 30 adjusting a space between the pair of bodies 10, a guide rail 40 guiding a movement of the bodies 10 when a space between the bodies 10 is adjusted, a key hole 50 formed in the extending screw 30 allowing the extending screw 30 to rotate when a rotational key is inserted thereinto and rotated, and a fixing part 60 combined with the arms 20 so as to be fixed to the teeth B of a patient. Also, the related art maxillary skeletal expander further includes hooks 70 allowing mini screws to be implanted therein to fix the bodies 10 to an upper jaw. The hooks 70 serve to fix the bodies 10 to an upper jaw when mini-screws are implanted therein, but the hooks 70 are disadvantageous in that they cannot guide the mini screws to be perpendicular to a direction in which the bodies 10 are expanded, resulting in that the mini-screws are implanted slantingly. Also, when the mini-screws are implanted in the hooks 70, the mini-screws are not vertically implanted during an implanting process, failing to properly transmit force when expanding, and the mini-screws may be loosened or the hooks 70 are bent.

SUMMARY

A maxillary skeletal expander using mini-screws is provided, which includes screw guide holes serving to guide mini-screws to be vertically implanted and having a predetermined size to properly transmit force to bones of an upper jaw when an extending screw are expanded.

According to an embodiment of the present invention for achieving the above objects, there is provided a maxillary skeletal expander including: a pair of bodies; an extending screw adjusting a space between the pair of bodies; guide rails having both sides inserted into the pair of bodies and guiding a movement of the bodies; a key hole integrally formed with the extending screw; screw insertion portions integrally formed with the bodies and having screw insertion holes guiding mini screws implanted to an upper jaw; arms having one end fixed to the bodies and the other end extending toward teeth; and a teeth fixing part integrally formed with the arms and fixed to teeth of a patient.

A height of the screw insertion portions may range from 1.5 mm to 3.0 mm.

The bodies may include a plurality of insertion holes allowing an extending screw, guide rails, and arms to be inserted therein, and the plurality of insertion holes and the screw holes are perpendicular to each other.

According to embodiments of the present invention, since the screw guide portions guiding an implantation direction of mini-screws are provided to allow the mini-screws to be implemented vertically, the mini-screws may be prevented from being released or a portion of mini-screws to which force is applied may be prevented from being bent. Also, since the mini-screws are vertically implanted, when a space between the bodies is extended, force may be properly transmitted to the bones of an upper jaw to effectively extend a maxillary arch.

Those skilled in the art will recognize additional features and advantages upon reading the following detailed description, and upon viewing the accompanying drawings.

BRIEF DESCRIPTION OF THE DRAWINGS

The elements of the drawings are not necessarily to scale relative to each other. Like reference numerals designate corresponding similar parts. The features of the various illustrated embodiments can be combined unless they exclude each other. Embodiments are depicted in the drawings and are detailed in the description which follows.

DETAILED DESCRIPTION

Hereinafter, a maxillary skeletal expander using mini-screws according to an embodiment of the present invention will be described in detail.

Figure 1:
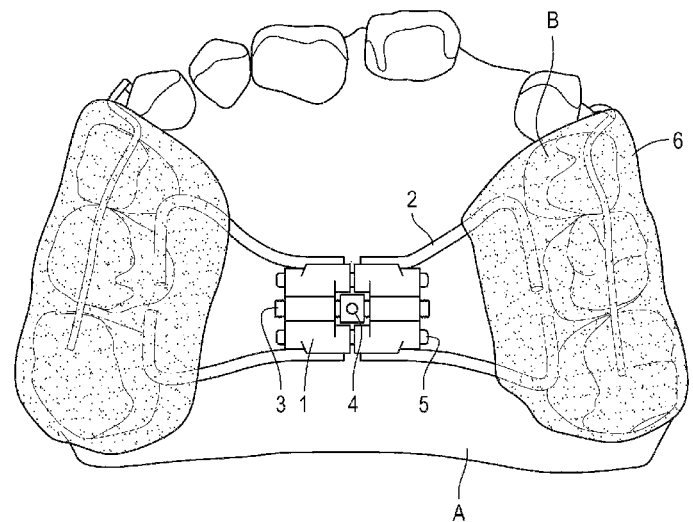
FIG. 1 is a view illustrating a related art maxillary skeletal expander.
Figure 2:
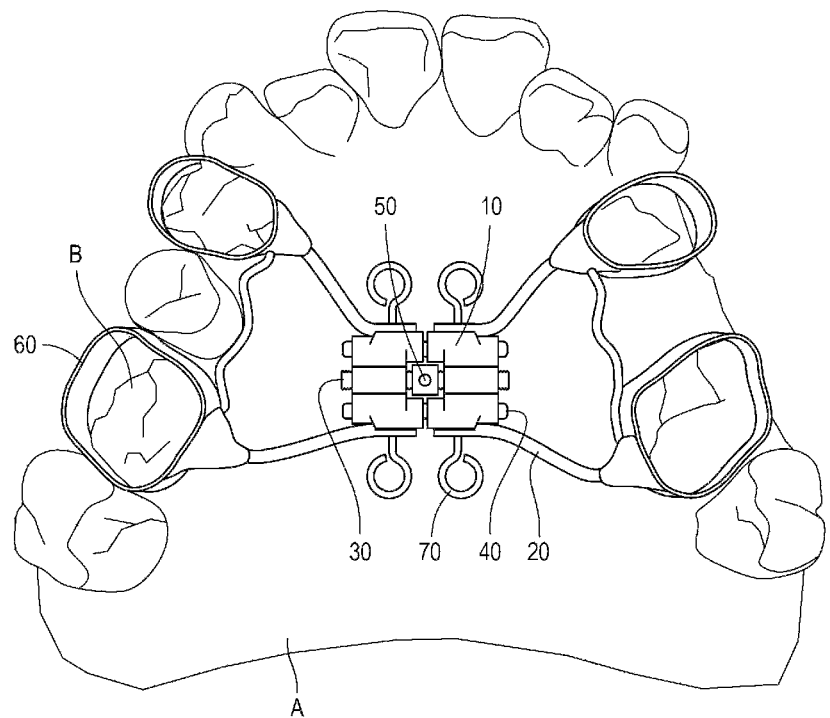
FIG. 2 is a view illustrating a related art maxillary skeletal expander using mini-screws.
Figure 3:
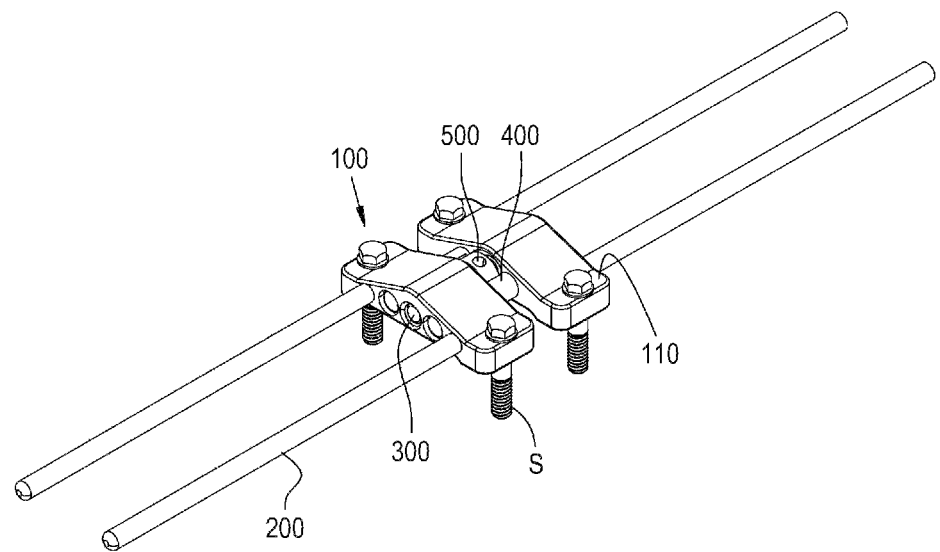
FIG. 3 is a perspective view illustrating a maxillary skeletal expander using mini-screws according to an embodiment of the present invention.
Figure 4:
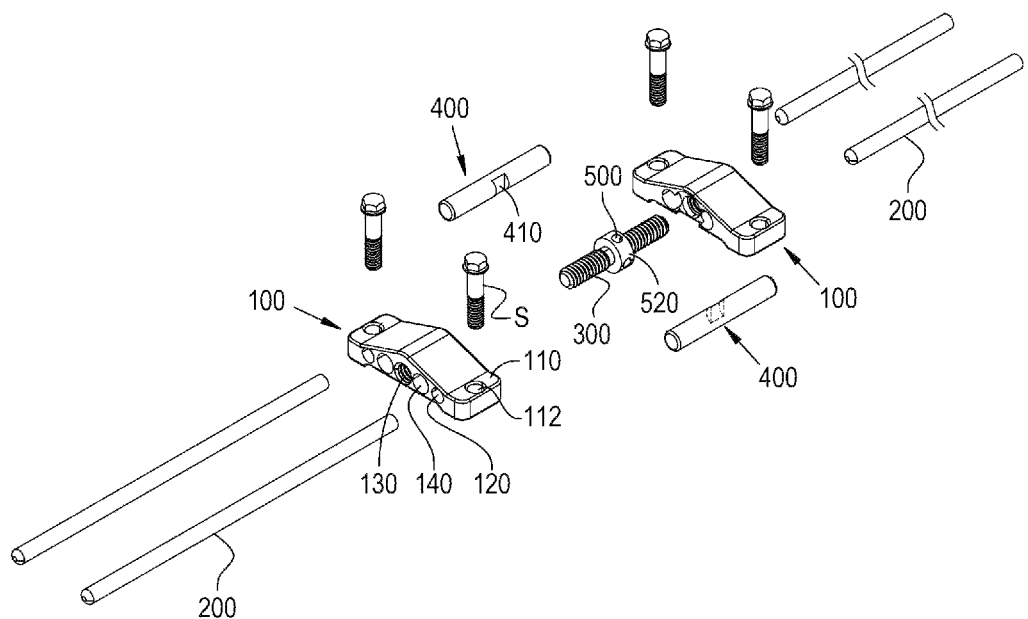
FIG. 4 is an exploded perspective view illustrating the maxillary skeletal expander using mini-screws according to an embodiment of the present invention.

FIG. 3 is a perspective view illustrating a maxillary skeletal expander using mini-screws according to an embodiment of the present invention, and FIG. 4 is an exploded perspective view illustrating the maxillary skeletal expander using mini-screws according to an embodiment of the present invention.

The maxillary skeletal expander using mini-screws according to an embodiment of the present invention includes a pair of bodies 100, arms 200 having one end fixed to the bodies 100 and the other end extending toward teeth B, an extending screw 300 having both side portions inserted into the pair of bodies 100 to adjust a space between the pair of bodies 100, guide rails 400 having both sides inserted into the pair of bodies 100 and guiding a movement of the bodies 100, a key hole 500 integrally formed with the extending screw 300, screw insertion portions 110 integrally formed with the bodies 100 and having screw insertion holes 112 guiding mini-screws S implanted to an upper jaw, and a teeth fixing part 600 integrally formed with the arms 200 and fixed to teeth of a patient.

The bodies 100 include a plurality of insertion holes 120, 130, and 140. Extending screw holes 130 are positioned at the center of the bodies 100 to allow the extending screw 300 to be inserted therein, a pair of rail insertion holes 140 are positioned on both sides of the extending screw insertion holes 130, and a pair of arm insertion holes 120 are positioned in outer sides of the pair of guide rail insertion holes 140. A direction in which the plurality of insertion holes 120, 130, and 140 are arranged and a direction in which the arms 200, the extending screw 300, and the guide rails 400 extend are perpendicular.

The extending screw 300 and the extending screw insertion holes 130 have threads engaging with each other, and the extending screw 300 may be rotated by inserting a key (not shown) into the key hole 500 formed in a central portion of the extending screw 300 and rotating the key (not shown). A space between the pair of bodies 100 may be widened or narrowed according to a direction in which the extending screw 300 is rotated. Hereinafter, for the description purposes, a direction in which the bodies 100 are moved when the extending screw, namely, a direction in which the arms 200, the extending screw 300, and the guide rails 400 extend, will be referred to as a horizontal direction, and a direction in which the plurality of insertion holes 120, 130, and 140 are arranged will be referred to as a vertical direction (or a forward/backward direction).

The maxillary skeletal expander using mini-screws is applied to the interior of an oral cavity, so it has a small overall size and components thereof are very small. Thus, a diameter of the extending screw 300 is also very small. Thus, it is not easy to form the key hole 500 having a size sufficiently maintained, without being broken, while receiving sufficient rotational force through a key (not shown). Thus, preferably, an extending portion 520 having a diameter greater than that of the screw portion inserted into the bodies 100 is formed at the center of the extending screw 300, and the key hole 500 is formed on the extending portion 520.

When the extending screw 300 is rotated to widen a gap between the bodies 100, the pair of guide rails 400 guide the bodies 100 to be moved smoothly. The guide rails 400 have a smooth rod-like shape without threads, unlike the extending screw 300, and positioned in front of and behind the extending screw 300. A gap between the pair of bodies 100 may be uniformly adjusted from a front end to a rear end thereof by means of the guide rails 400. Also, in order to avoid interference by the extending portion 520 the rails 400 have extending portion avoidance portions 410. The extending portion avoidance portions are recesses having a size and a shape sufficient for avoiding frictional contact with the extending portion 520.

The arms 200 are positioned in outer side of the guide rails. Namely, the arms 200 are positioned in front of the guide rails 400 positioned in front and are positioned in the rear of the guide rails 400 positioned in the rear. The teeth fixing part 600 as described hereinafter (please refer to FIG. 5) may be combined to the ends of the arms 200 to fix the maxillary skeletal expander using the mini-screws S to the upper jaw. Unlike the guide rails 400, the arms 200 are fixed to the bodies 100, and a pair of arms 200 are combined with a single body 100, and thus, a total of two pairs of arms, i.e., four arms 200, are provided.

Meanwhile, the bodies 100 have the screw insertion portion 110 formed in outer side of a plurality of the insertion holes 120, 130, and 140. Namely, the bodies 100 have the screw insertion portions formed in front of and in the rear of the plurality of insertion holes 120, 130, and 140. The screw insertion holes 112 are formed in the screw insertion portions 110 and may fix the bodies 100 to bones of a maxillary arch by using mini-screws S. A direction in which the mini-screws S are implanted is perpendicular to a direction in which the plurality of insertion holes 120, 130, and 140 are arranged, and is also perpendicular to a direction in which the bodies 100 are moved. Namely, if it is assumed that a movement direction of the bodies 100 is a horizontal direction and an arrangement direction of the plurality of insertion holes 120, 130, and 140 is a forward/backward direction when the extending screw 300 is rotated, an implantation direction of the mini-screws S may be a vertical direction. By implanting the mini-screws S such that they are perpendicular to the movement direction of the bodies 100, the mini-screws S may be prevented from being released the screw insertion portions 110 are prevented from being bent, while the mini-screws S are forced. Also, since the mini-screws S are vertically implanted in the bones of the mixillary arch, when a space between the bodies 100 is extended, force may be properly transmitted to the bones of the maxillary arch to effectively extend the maxillary arch.

A height of the screw insertion holes 112, namely, a thickness of the screw insertion portions 110 may range from 1.5 mm to 3.0 mm. If a height of the screw insertion hole 112 is smaller than 1.5 mm, namely, when a thickness of the screw insertion hole 112 is smaller than 1.5 mm. the screw insertion portions 110 may be bent or broken when forced and it is difficult to accurately guide the mini-screws S to be implemented in a vertical direction. Also, if a height of the screw insertion holes 112 is greater than 3.0 mm, namely, when a thickness of the screw insertion holes 110 is greater than 3.0 mm, the screw insertion holes are excessively protruded within the cavity to cause a patient's discomfort.

Figure 5:
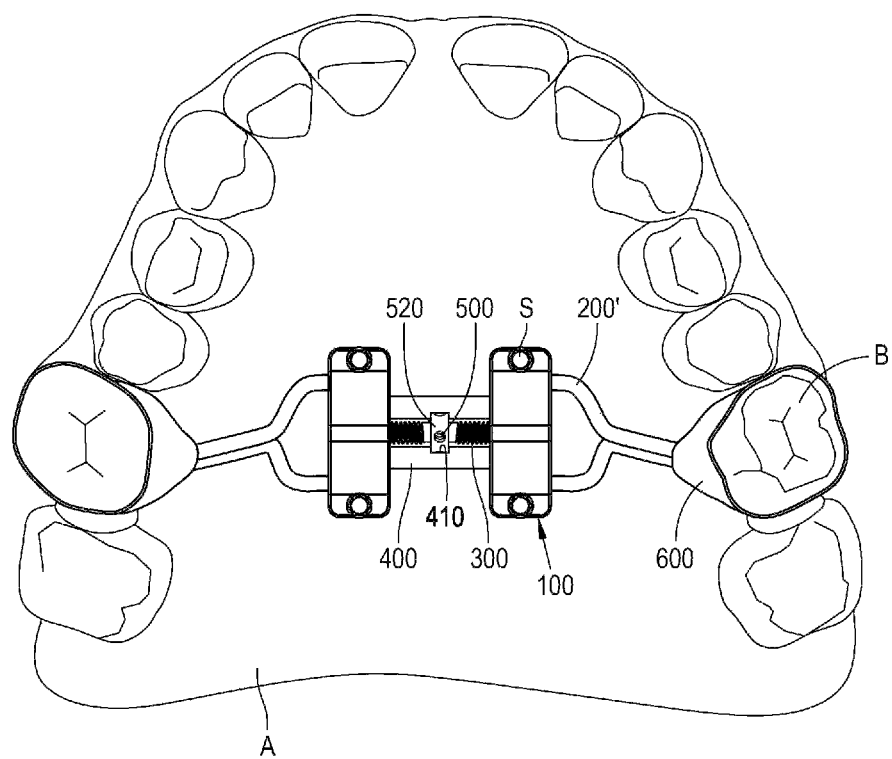
FIG. 5 is a view illustrating an example of application of the maxillary skeletal expander using mini-screws according to an embodiment of the present invention to an upper jaw of a patient.

FIG. 5 is a view illustrating an example of application of the maxillary skeletal expander using mini-screws according to an embodiment of the present invention to an upper jaw of a patient.

When the maxillary skeletal expander using mini-screws is applied to the maxillary arch to a patient, arms 200' are deformed to fit an upper jaw of the patient. Also, a pair of arms 200' are formed to be spaced apart from one another in a single body 100, and the pair of arms 200' are combined to a single teeth fixing part 600. The teeth fixing part 600 is fixed to the teeth B of a patient, and here, since the mini-screws S are not sufficient to fix the body 100, fixing force is additionally applied to fix the body 100.

Spatially relative terms such as "under", "below", "lower", "over", "upper" and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc. and are also not intended to be limiting. Like terms refer to like elements throughout the description.

As used herein, the terms "having", "containing", "including", "comprising" and the like are open-ended terms that indicate the presence of stated elements or features, but do not preclude additional elements or features. The articles "a", "an" and "the" are intended to include the plural as well as the singular, unless the context clearly indicates otherwise.

With the above range of variations and applications in mind, it should be understood that the present invention is not limited by the foregoing description, nor is it limited by the accompanying drawings. Instead, the present invention is limited only by the following claims and their legal equivalents.

What is claimed is:

1. A maxillary skeletal expander, comprising:
   a pair of bodies configured to be fixed directly to a palatine bone;
   an extending screw configured to adjust a space between the pair of bodies;
   a pair of guide rails, each guide rail having a first end and second end, wherein the first end and second end of each of the guide rails is inserted into the pair of bodies for guiding a movement of the bodies;
   a key hole integrally formed with the extending screw;
   two pairs of arms, each pair of arms having one end fixed to one of the bodies and the other end extending toward teeth; and
   a teeth fixing part integrally formed with each pair of the arms and configured to be fixed to teeth of a patient,
   wherein each body of the pair of bodies has screw insertion holes for guiding micro-screws to be implanted to the palatine bone in order to fix the bodies, and which are formed at both sides of each body.

2. The maxillary skeletal expander of claim 1, wherein a height of the screw insertion holes ranges from 1.5 mm to 3.0 mm.

3. The maxillary skeletal expander of claim 1, wherein the bodies include a plurality of insertion holes allowing the extending screw, the guide rails, and the arms to be inserted therein, and wherein the plurality of insertion holes and the screw insertion holes are perpendicular to each other.

* * * * *